US009283012B2

(12) United States Patent
Brand

(10) Patent No.: US 9,283,012 B2
(45) Date of Patent: Mar. 15, 2016

(54) STORAGE UNIT, SET AND SURGICAL CONTAINER

(75) Inventor: Stefan Brand, Basel (CH)

(73) Assignee: MEDARTIS AG, Basel (CH)

( * ) Notice: Subject to any disclaimer, the term of this patent is extended or adjusted under 35 U.S.C. 154(b) by 228 days.

(21) Appl. No.: 13/118,864

(22) Filed: May 31, 2011

(65) Prior Publication Data

US 2011/0297571 A1  Dec. 8, 2011

(30) Foreign Application Priority Data

Jun. 3, 2010  (EP) .................................... 10164870

(51) Int. Cl.
  *B65D 83/10*  (2006.01)
  *A61B 17/86*  (2006.01)
  *A61B 19/02*  (2006.01)

(52) U.S. Cl.
  CPC ........... *A61B 17/865* (2013.01); *A61B 19/0256* (2013.01); *A61B 19/0271* (2013.01)

(58) Field of Classification Search
  CPC .. B65D 85/24; A61B 19/026; A61B 19/0271; A61B 19/0256; A47F 7/00; A61L 2/00
  USPC ......... 206/370, 468, 369, 339, 438, 338, 341, 206/347, 380; 606/86 R, 300, 286, 288, 290, 606/295; 220/512; 211/85.13; 11/370, 468, 11/369, 339, 438
  See application file for complete search history.

(56) References Cited

U.S. PATENT DOCUMENTS

| 3,868,016 A | | 2/1975 | Szpur | |
|---|---|---|---|---|
| 5,433,929 A | * | 7/1995 | Riihimaki et al. | 422/297 |
| 5,540,901 A | | 7/1996 | Riley | |
| 5,759,502 A | * | 6/1998 | Spencer et al. | 422/300 |
| 5,829,591 A | * | 11/1998 | Lyons | 206/373 |
| 7,857,129 B2 | * | 12/2010 | Iaconi-Forrer et al. | 206/339 |
| 7,931,143 B1 | * | 4/2011 | Lin | 206/373 |
| 8,162,138 B2 | * | 4/2012 | Bettenhausen et al. | 206/339 |
| 8,317,021 B2 | * | 11/2012 | Christopher | 206/375 |
| 2001/0054563 A1 | * | 12/2001 | Lang et al. | 206/369 |
| 2006/0016706 A1 | * | 1/2006 | Chen | 206/379 |
| 2006/0243616 A1 | | 11/2006 | Caron | |

FOREIGN PATENT DOCUMENTS

| DE | 102006062688 | 10/2007 |
|---|---|---|
| EP | 1972290 | 9/2008 |
| WO | 2005/092231 | 10/2005 |
| WO | 2009/024189 | 2/2009 |

* cited by examiner

*Primary Examiner* — Luan K Bui
*Assistant Examiner* — Rafael Ortiz
(74) *Attorney, Agent, or Firm* — Davis & Bujold PLLC; Michael J. Bujold

(57) ABSTRACT

A storage unit for storing and/or making available at least one carrier for at least one surgical item, in particular for at least one bone screw. The carrier can be brought to a holding position and to a release position, the carrier being held by the storage unit in the holding position and being released or releasable from the storage unit in the release position. The storage unit has at least one release part. The carrier can be brought from the holding position to the release position by actuation of the release part. The invention further relates to a set containing at least one such storage unit and at least one carrier for at least one surgical item, in particular for at least one bone screw. The invention moreover relates to a surgical container containing at least one storage unit and/or at least one set.

23 Claims, 16 Drawing Sheets

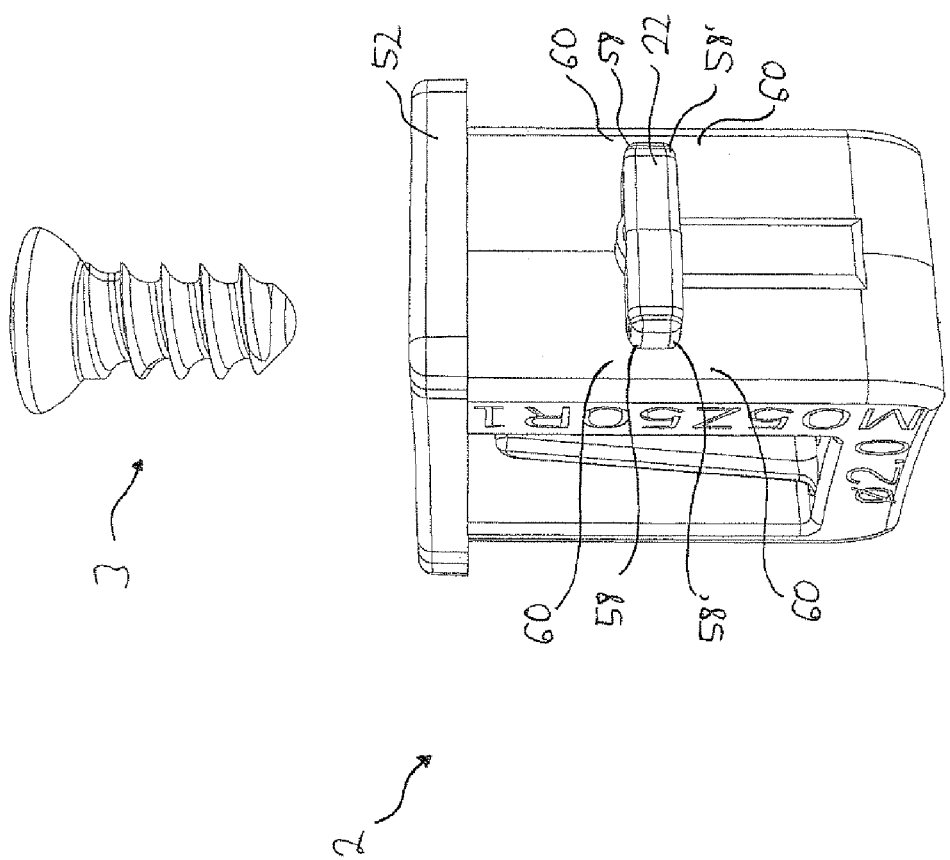

STORAGE UNIT, SET AND SURGICAL CONTAINER

The present invention relates to a storage unit for storing and/or making available at least one carrier for at least one surgical item, to a set containing at least one such storage unit and a carrier, and to a surgical container.

A storage unit of the type in question is described, for example, in EP 1 972 290. This storage unit contains a rectangular plate with a multiplicity of oval recesses. By means of a locking connection, carriers for bone screws can be inserted into these recesses. To remove the carriers from the storage unit, the carriers have to be gripped by the fingers and pulled out with a force that overcomes the force exerted by the locking means. This is very awkward on account of the small size of the carriers. A further disadvantage of this known storage unit is that it is not immediately apparent in which sequence the carriers with screws have been inserted into the storage unit. Therefore, without further organizational measures, it is not possible to remove the screws and carriers from the storage unit in the sequence in which they were inserted therein. Moreover, the known carrier allows a screw to be easily reinserted into the carrier, such that no traceability is guaranteed. Moreover, the known carrier takes up a great deal of space.

A further storage unit of the type in question for carriers is described in WO 2005/092231. Each of the carriers has a cover preventing the bone screw from falling out. This storage unit comprises a tray with a large number of slide rails, which are arranged next to one another and along which the individual carriers with inserted bone screws are movable. By moving them along the slide rails to an open end of the rail, the carriers can be separated from the tray. Abutment lugs are arranged at these open ends. With a suitable length of the bone screws, the carriers can only be removed when the screw has already been withdrawn. It is not possible to tell from the known tray in which sequence the carriers with screws have been inserted. Therefore, without further organizational measures, it is not possible to guarantee that the screws are removed in the sequence in which they were inserted. Moreover, in the case of a carrier whose cover has been removed, a bone screw can easily fall out of the carrier in the event of accidental tilting of the storage unit.

Finally, a storage unit with guide rails is also disclosed in WO 2009/024189. In this storage unit too, the carriers can only be removed by being directly gripped and pulled out of the guide rails, which proves extremely difficult to do because of the small size of the carriers. Moreover, in this storage unit too, it is not possible to tell in which sequence the carriers with the bone screws have been inserted.

It is therefore an object of the present invention to overcome the disadvantages of the storage units known from the prior art. In particular, a storage unit for carriers for a surgical item is to be made available from which the carriers can be more easily removed, but without the carriers being able to accidentally fall out.

This object is achieved by a storage unit for storing and/or making available at least one carrier, preferably several carriers, for at least one surgical item, in accordance with independent claim 1. The surgical item can be a bone screw, for example. The carrier can be brought to a holding position and to a release position, the carrier being held by the storage unit in the holding position and being released or releasable from the storage unit in the release position.

The expression holding position is not to be understood as meaning that the carrier in this position cannot be released at all from the storage unit. It is only essential that the carrier in the release position can be released from the storage unit by less force than is the case in the holding position. The extent of the holding force present in the holding position can, for example, be such that the carrier, even in a tilted position of the storage unit, does not fall out of the latter due to its own gravity.

According to the invention, the storage unit has at least one release part, and the carrier can be brought from the holding position to the release position by actuation of the release part. Thus, as long as the release part is not actuated, the carrier remains in the holding position, in which it is held by the storage unit. It is only after the release part has been actuated that the carrier is or can be released from the storage unit. In particular, therefore, the carrier itself does not have to be gripped in order to move it to the release position counter to the holding force that is present in the holding position. In the release position, the carrier can then be very easily removed from the storage unit.

In advantageous embodiments, the storage unit has at least one main body, in relation to which the release part is movable. Thus, by movement of the release part in relation to the main body, a carrier can be brought from the holding position to the release position, such that the carrier can be removed from the storage unit. The release part is or can be connected directly or indirectly to the main body.

The main body can contain or consist of a plastic known per se, for example PPSU or PEEK. It can be produced, for example, by injection molding.

The storage unit, in particular the main body, has at least one guide rail, along which the carrier is arranged to be movable in a guide direction. The storage unit preferably has at least two guide rails. In particular, the storage unit can have an upper guide rail and a lower guide rail arranged one above the other. Here, "one above the other" means that the upper guide rail and the lower guide rail are spaced apart from each other in a direction corresponding to a removal direction in which the carrier can be released from the storage unit. An upper guide rail and a lower guide rail allow a guide projection on the carrier to be guided in the space between the upper guide rail and the lower guide rail.

The storage unit is preferably designed in such a way that, when it is in the intended orientation, the guide direction lies in a horizontal plane. For example, in the case of a substantially rectangular storage unit, an intended orientation can be one in which the storage unit is placed with its largest surface on a horizontal support. Such a plane of the storage unit is referred to here and hereinbelow as the main plane.

The storage unit can be designed in such a way that the carrier, in the release position, can be released from the storage unit by movement in a removal direction, which lies substantially perpendicular to the guide direction. If, for example, the guide direction lies in the main plane of the storage unit, the carrier can be removed upward in a vertical direction when the storage unit is in the intended orientation. The carrier does not then have to be removed in the direction of the continuation of the guide rails. Moreover, if a further guide rail is arranged next to the guide rail, the carrier also does not have to be removed in the direction of this further guide rail. Several guide rails can therefore be arranged at a relatively short distance from one another in the storage unit. Both effects result in more carriers, and therefore more surgical items, being able to be made available per surface area in the storage unit.

The release part is preferably arranged in an end area of the guide rail. It is likewise preferable that, by actuation of the release part, the carrier can be brought from the holding position to the release position only in a removal area. In this case, the removal area forms only a part of the storage unit, which part can be arranged in particular in an end area of the guide rail. This configuration means that the carriers can be removed from the storage unit only in a defined removal area. If this removal area is arranged in an end area of the guide rail, the carriers can be removed only in this end area. It is thus possible to ensure that the carriers can be removed from the storage unit only in a clearly defined sequence.

In preferred embodiments, the release part is or can be connected directly or indirectly in a movable manner to an actuating element in such a way that, upon actuation of the actuating element, the release part is actuated. The release part in this case is or can be connected directly or indirectly to the actuating element. In such a design, therefore, the release part does not have to be actuated directly, and, instead, only the actuating element has to be actuated. This can serve, for example, for a better transfer or transmission of force to the carrier.

The actuating element can display letters, numbers or symbols, which identify the surgical items received in the carrier, for example the diameter and the length of bone screws. For several guide rails containing carriers with different surgical items, it is possible, for example, to use the same release part in each case, but different actuating elements.

In preferred embodiments, the storage unit is designed in such a way that, upon actuation of the release part, the carrier can be brought from the holding position to the release position on account of a direct contact between the carrier and the release part. In particular, this can be achieved by contact between at least one first contact surface of the release part and at least one second contact surface of the carrier.

Particularly preferably, the first contact surface is oriented substantially in the removal direction, and the second contact surface, in the holding position, faces counter to the removal direction. In this way, the force needed for the transfer from the holding position to the release position can be applied particularly effectively.

Alternatively to direct contact between the carrier and the release part, the carrier can also be moved from the holding position to the release position indirectly. For example, it is conceivable that the carrier is held in the holding position by a spring, and, by movement of the release part, the spring is moved in such a way that it permits the removal of the carrier. The carrier can preferably be held in the holding position by an in particular elastic holding spring, which clamps the carrier in a direction lying substantially perpendicular to a removal direction.

In advantageous embodiments, the release part and/or the actuating element are supported, by means of at least one tension spring, in relation to the main body or to a base part connected fixedly to the main body. To actuate the release part and/or the actuating element, the spring force of this tension spring then has to be overcome in order to bring the carrier from the holding position to the release position. By a suitable choice of the properties of the tension spring, it is thus possible to ensure that the carrier is brought from the holding position to the release position only when a force is exerted that exceeds a predetermined threshold force. Inadvertent release of the carrier can thus be avoided. Moreover, the tension spring can have the effect that the release part and/or the actuating element return automatically to the original position after the carrier has been removed.

Advantageously, the release part and/or the actuating element are mounted pivotably in relation to the main body. This type of construction is particularly simple. In particular, the release part and/or the actuating element can be pivoted about a pivot axis lying substantially perpendicular to the guide direction and/or substantially perpendicular to the removal direction. This construction too is very simple but nevertheless effective.

In particularly preferred embodiments, the release part is mounted pivotably in relation to the main body, while the actuating element is movable in a substantially linear manner in relation to the main body, in particular substantially parallel to the removal direction. By means of the movable connection between release part and actuating element, a linear movement of the actuating element can then be converted into a pivoting movement of the release part.

The release part, the base part and the actuating element can contain or consist of plastics known per se, for example PPSU or PEEK. They can be produced by methods known per se, for example by injection molding.

The storage unit preferably has at least one receiving area in which the carrier can be received by the storage unit. In particular, the carrier can be received by the storage unit by movement in a direction lying substantially perpendicular to the guide direction and/or substantially counter to the removal direction. This construction is also particularly compact, since the carrier can be inserted into the storage unit perpendicularly with respect to a main plane in which the guide direction extends.

If the guide rail contains only a single receiving area, arranged in one of the end areas of the guide rail, a carrier can be received by the storage unit only at this one location. If several carriers have been received, the sequence of insertion is then immediately apparent. Moreover, if the storage unit contains only a single removal area, a carrier can be removed from the storage unit only at this one location. Therefore, the carriers can be removed from the storage unit only in the sequence in which they were received by the storage unit.

A further aspect of the invention concerns a set containing at least one storage unit as described above and at least one carrier, preferably several carriers, for at least one surgical item. The surgical item in question can be a bone screw, for example. The storage unit can have one, several or all of the above-described features and thus have the respective advantages explained above.

At least one of the carriers, preferably several of the carriers, particularly preferably all of the carriers are received by the storage unit. In particular, the carrier or carriers can be located in the holding position.

The carrier can be designed to receive an elongate surgical item having a longitudinal axis, the removal direction being substantially parallel to the longitudinal axis. The elongate surgical item in question can be a bone screw, for example. A particularly compact configuration is possible if the item can be removed in the direction of its longitudinal axis from the carrier.

Particularly preferably, at least one surgical item is inserted in the carrier, in particular at least one bone screw.

A further aspect of the invention concerns a surgical container, which contains at least one storage unit as described above and/or at least one set as described above. The storage unit and/or the set can have one, several or all of the above-described features and thus have the respective advantages explained above.

The invention is explained below on the basis of an illustrative embodiment and with reference to several drawings, in which:

FIGS. 3a, 3b show two perspective views of a carrier with a bone screw;

Figure 1:
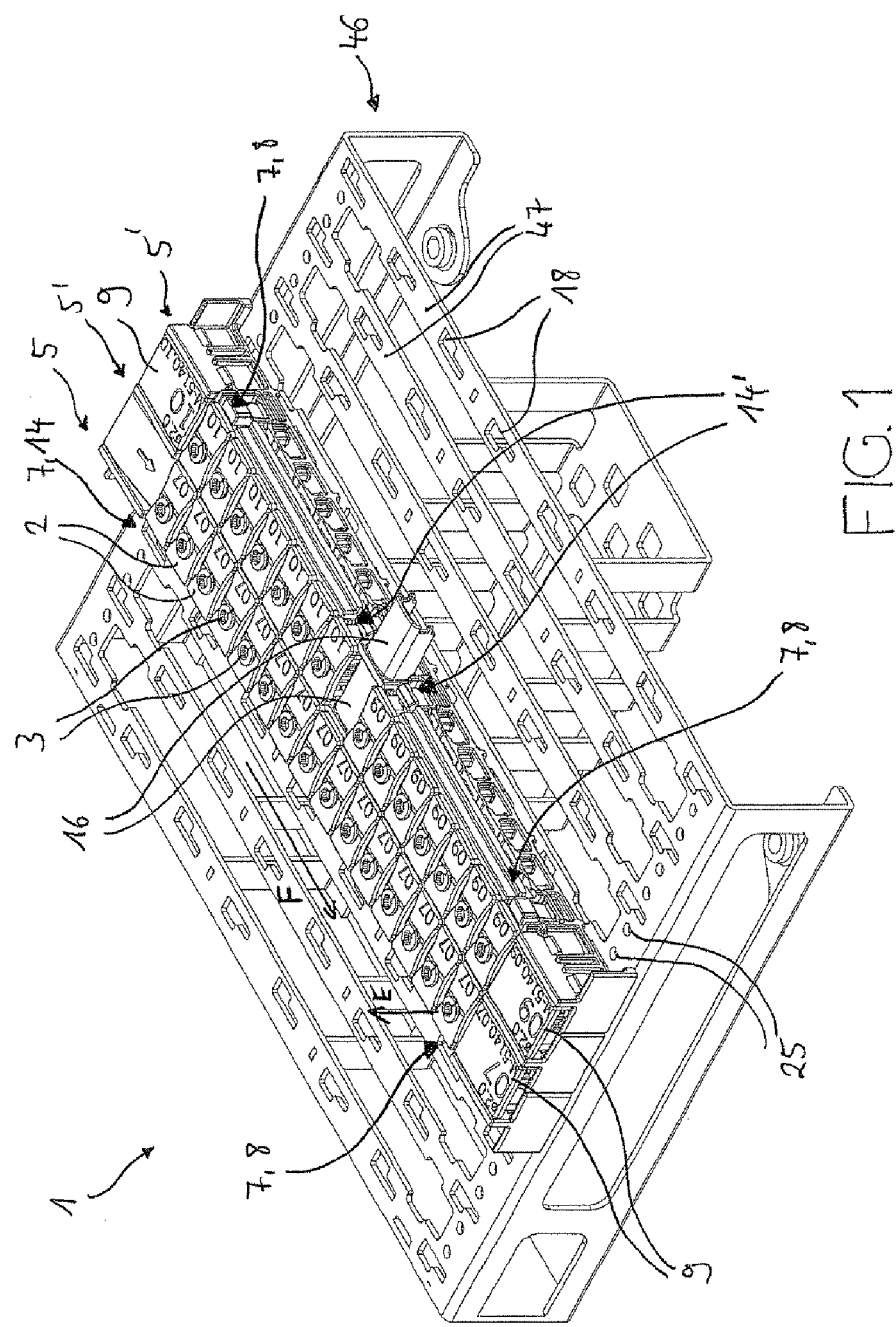
FIG. 1 shows a perspective view of a storage unit according to the invention with carriers received therein.

FIG. 1 is a perspective view of a storage unit 1 according to the invention for storage and presentation. Such a storage unit 1 can be arranged in a surgical container (not shown here). The storage unit 1 contains a main stand 46 with a plurality of webs 47 extending parallel to one another. Each of the webs 47 has several holding openings 18. A first main body 5 and two second main bodies 5' are in each case secured on one of the webs 47. For this purpose, the main bodies 5, 5' have several holding hooks (not shown) which engage in the holding openings 18 (cf. FIGS. 5 to 8 below). Moreover, in the edge area, the main stand 46 also has several openings 25, the function of which is explained further below.

Several carriers 2, each with a bone screw 3 inserted therein, are received between two adjacent main bodies 5, 5'. The carriers 2, together with the bone screw 3 inserted therein, are movable along guide rails (not shown here) in a guide direction F. The storage unit 1 has an actuating element 9 in each of three end areas 7 of the guide rails. On a cover plate of the actuating element 9, information is shown that identifies the bone screws 3. The actuating elements 9 are located in removal areas 8 in which the carriers 2 can be removed in a removal direction E, as is described in detail below. The carriers 2, with or without bone screw 3, can be received by the storage unit 1 in three receiving areas 14, 14'. One of the receiving areas 14 is located in an end area 7 of the guide rails. The two other receiving areas 14' are located in a middle area and are separated from each other by a separating element 16. In the example shown, screws of a first kind ("09") are arranged to the left of the separating element 16 and screws of a second kind ("10") are arranged to the right of the separating element 16.

Figure 2:
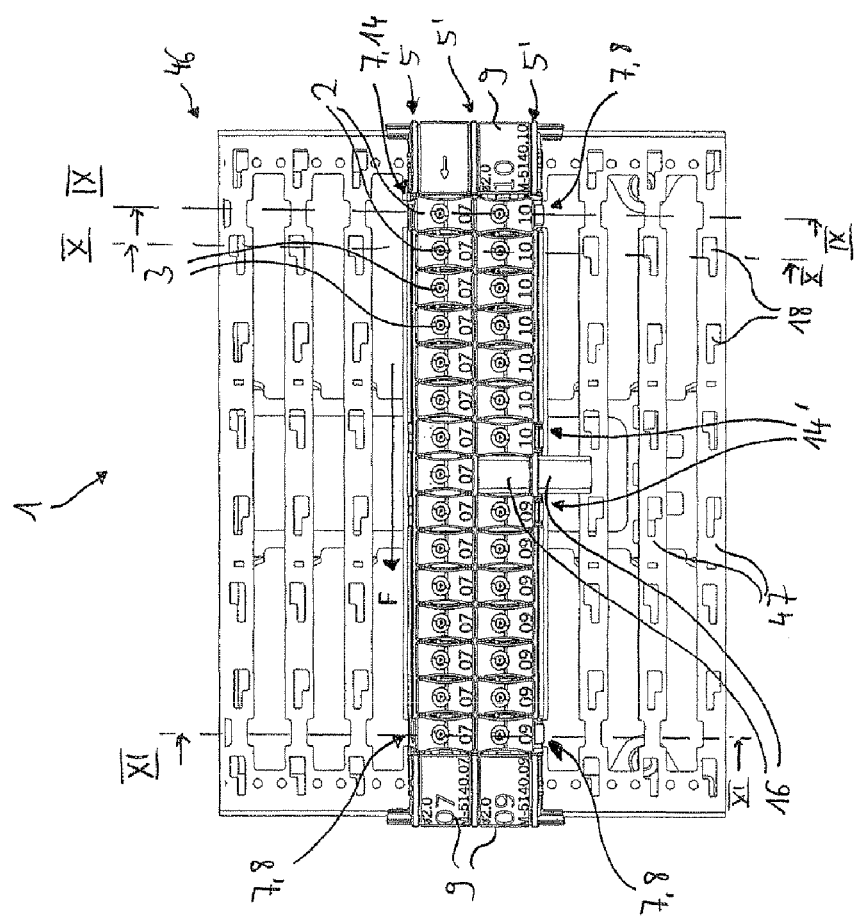
FIG. 2 shows the storage unit according to FIG. 1 in a plan view.
Figure 9:
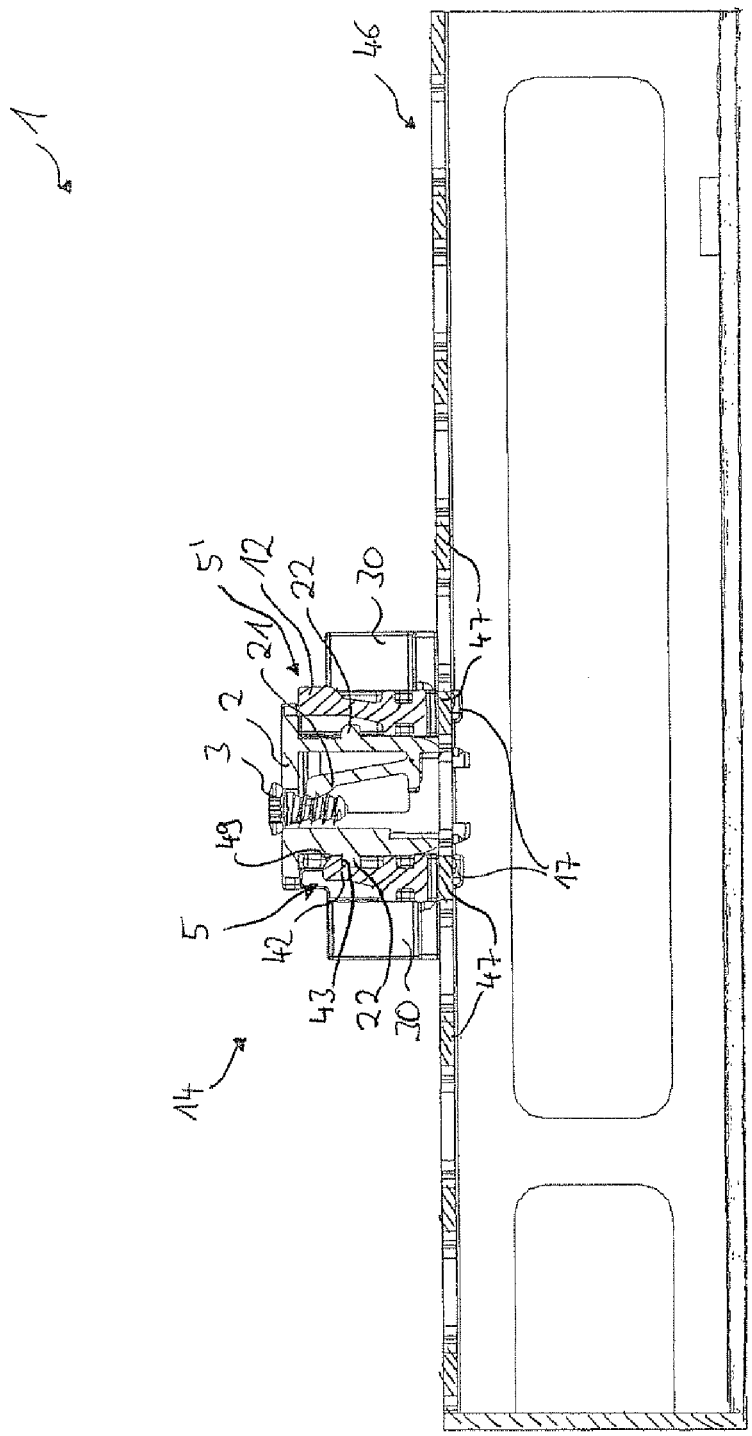
FIG. 9 shows the storage unit in a sectional side view through a receiving area.
Figure 10:
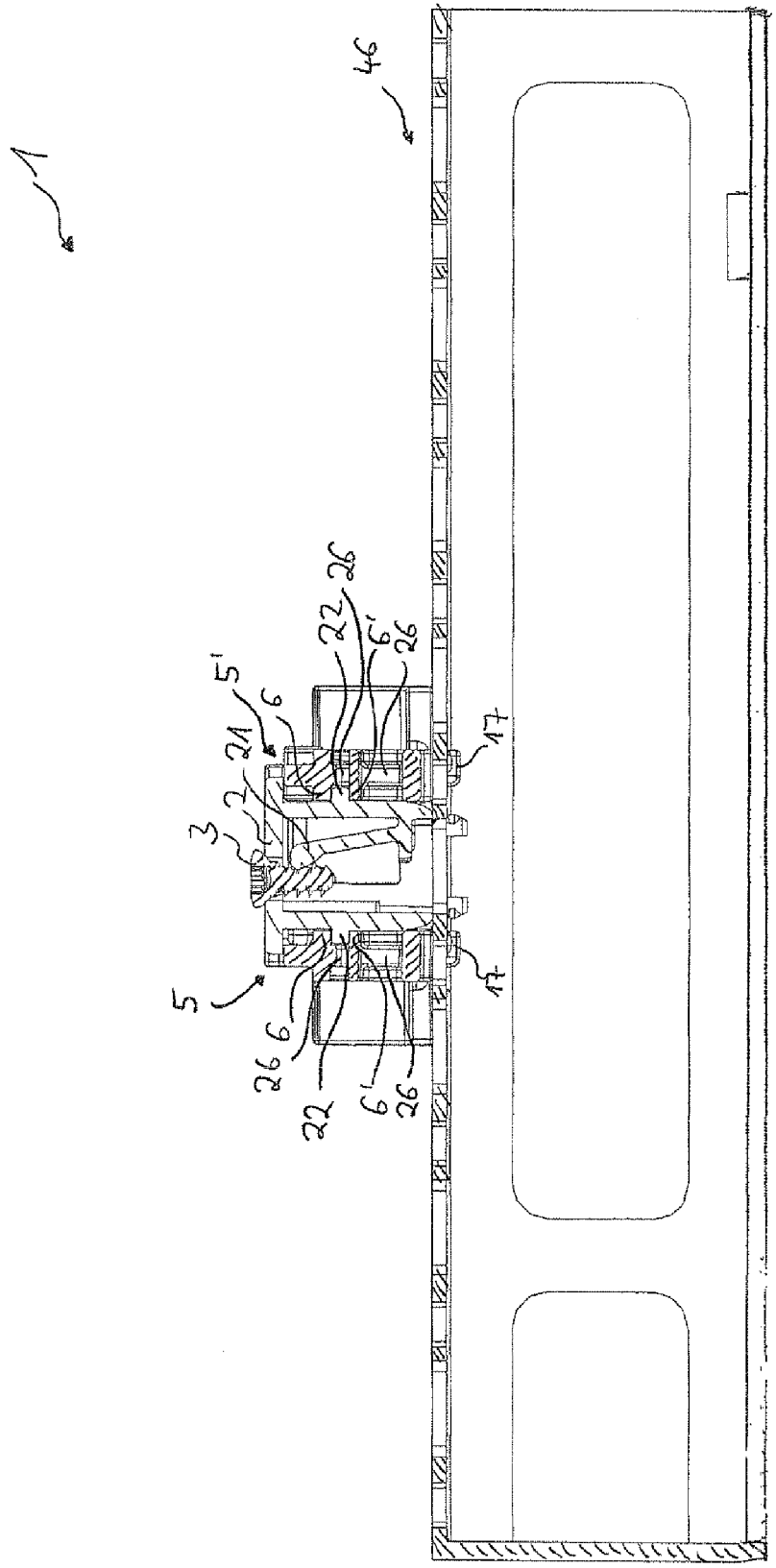
FIG. 10 shows the storage unit in a sectional side view through a middle area.
Figure 11:
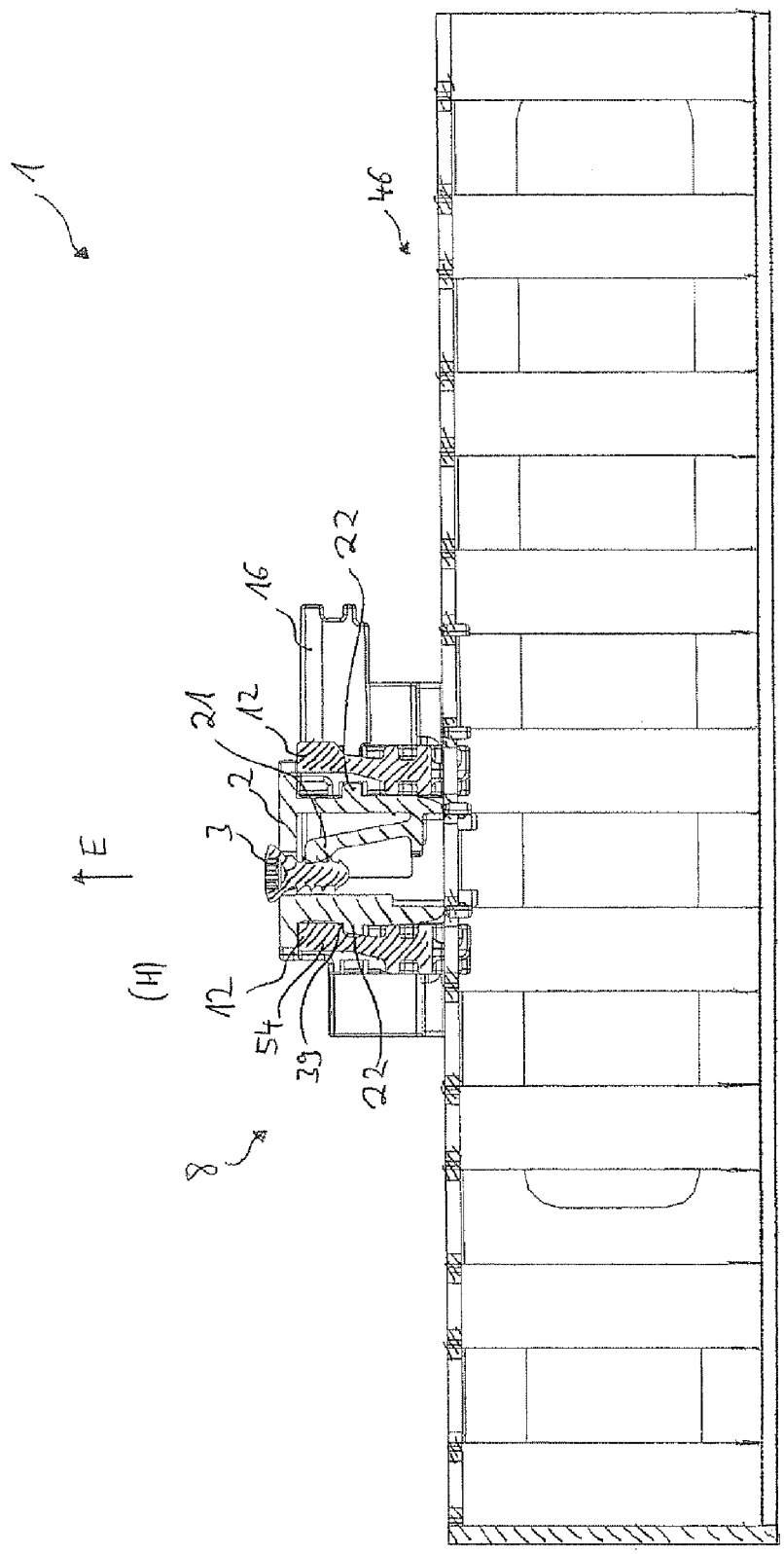
FIG. 11 shows the storage unit in a sectional side view through a removal area.

FIG. 2 shows a plan view of the storage unit 1. Sectional views along the lines IX, X and XI are shown in FIGS. 9, 10 and 11, respectively.

Figure 3A:
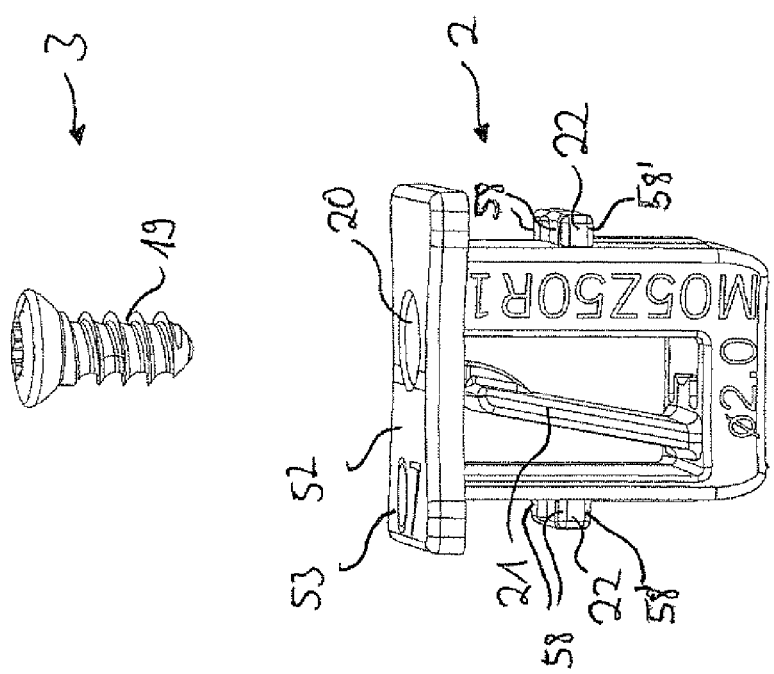

FIGS. 3a and 3b show a carrier 2 and a bone screw 3. According to FIG. 3a, the carrier 2 has, on a top face 52, a circular receiving opening 20 into which the screw shank 19 of the bone screw 3 can be inserted. In the received position, the bone screw 3 can be held by a holding tongue 21 (cf. also FIGS. 9 to 11). The top face 52 of the carrier 2 contains a marking 53, which contains technical information concerning the bone screw 3. On each of two opposite sides, the carrier 2 has a guide projection 22, by means of which the carrier 2 is movable along the guide rails of the storage unit 1. Each of the guide projections 22 has, on its surface, two upper edges 58 and two lower edges 58', the function of which is explained below in connection with FIGS. 9 and 11.

FIG. 3b shows another perspective view of the carrier 2 and of the bone screw 3. The guide projection 22 visible here and the opposite guide projection, which is not visible here, extend across only part of the total width of the carrier 2. The side wall of the carrier 2 contains, laterally in relation to the guide projection 22, contact areas 60 which, by means of contact with mating contact areas of the main bodies 5, 5', support the carrier 2 against tilting in the receiving areas 14, 14' and in the removal areas 8 (cf. description of FIGS. 9 and 11 below).

Figure 4:
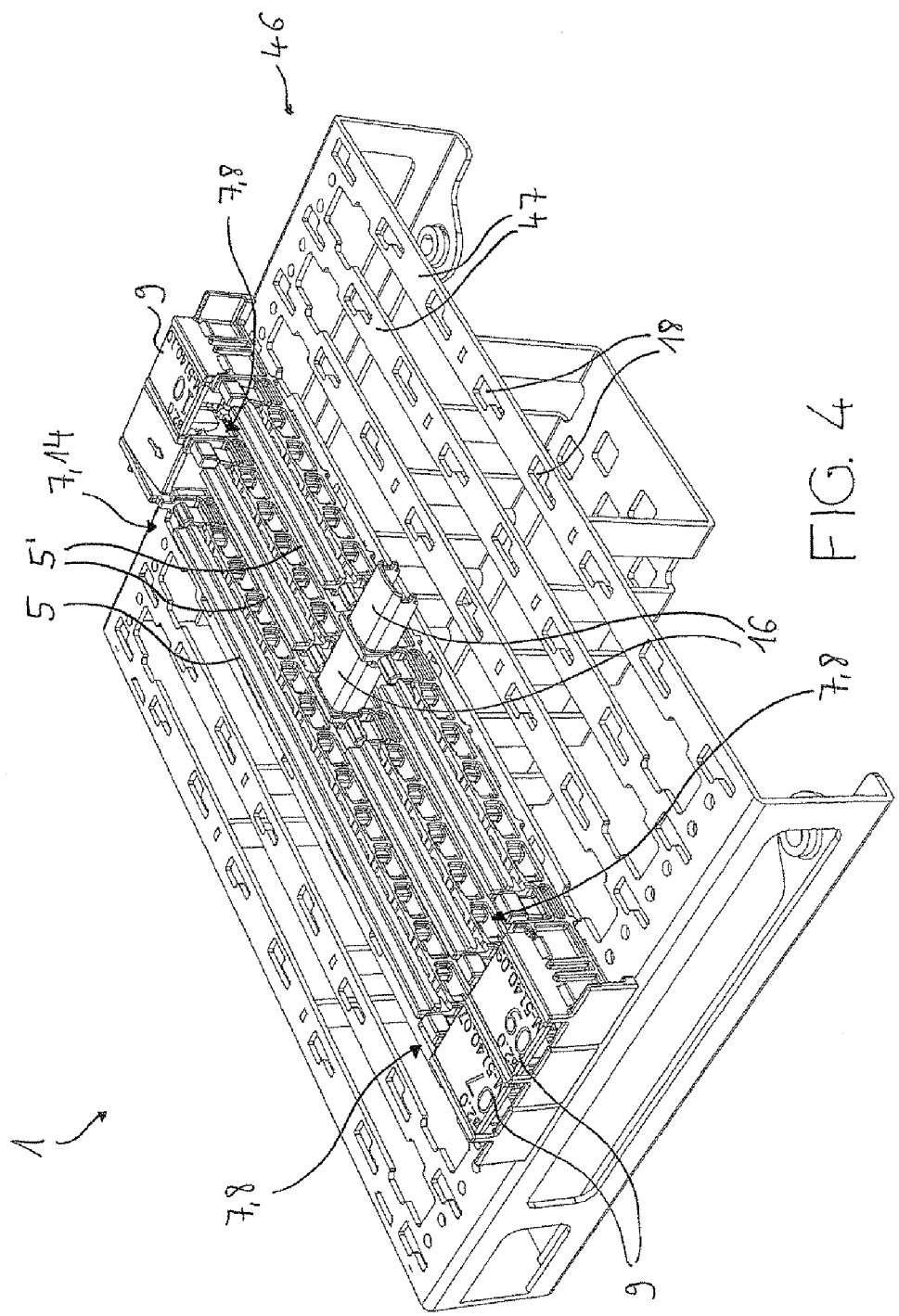
FIG. 4 shows the storage unit according to FIGS. 1 and 2 without carriers.

FIG. 4 shows a perspective view of the storage unit from FIGS. 1 and 2 without carriers 2 and bone screws 3. This figure shows the first main body 5 and, separate from the latter, the second main bodies 5', which are described in more detail in the following figures. Both main bodies 5, 5' have a length of 114 mm, a width of 10 mm and a height of 9 mm. They can be made of PPSU or PEEK and, for example, produced by injection molding.

Figure 5:
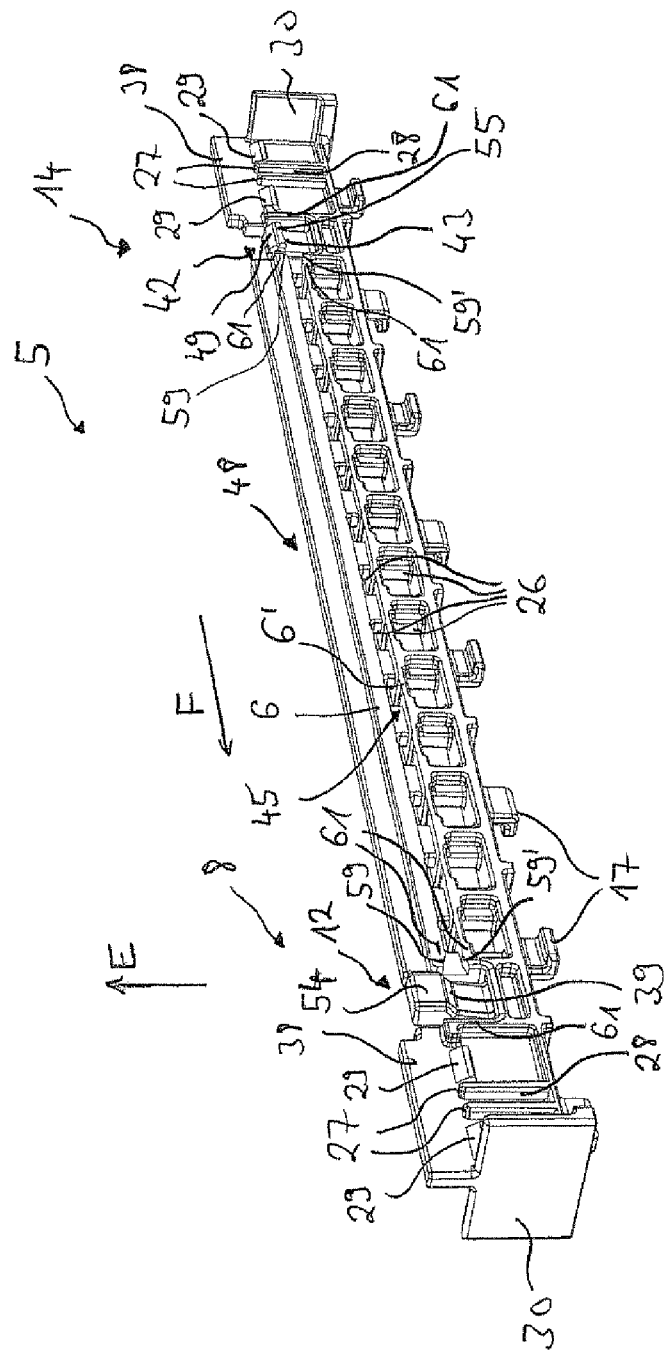
FIG. 5 shows a first main body of the storage unit in a first perspective view.

FIG. 5 shows the main body 5 in a perspective view. The main body 5 is of elongate shape and has, at each of its two ends, an approximately rectangular end piece 30, which extends perpendicular to the longitudinal extent of the main body 5. A middle piece 48 extends between the two end pieces 30. An intermediate piece 38 is located between the middle piece 48 and each of the two end pieces 30.

Figure 6:
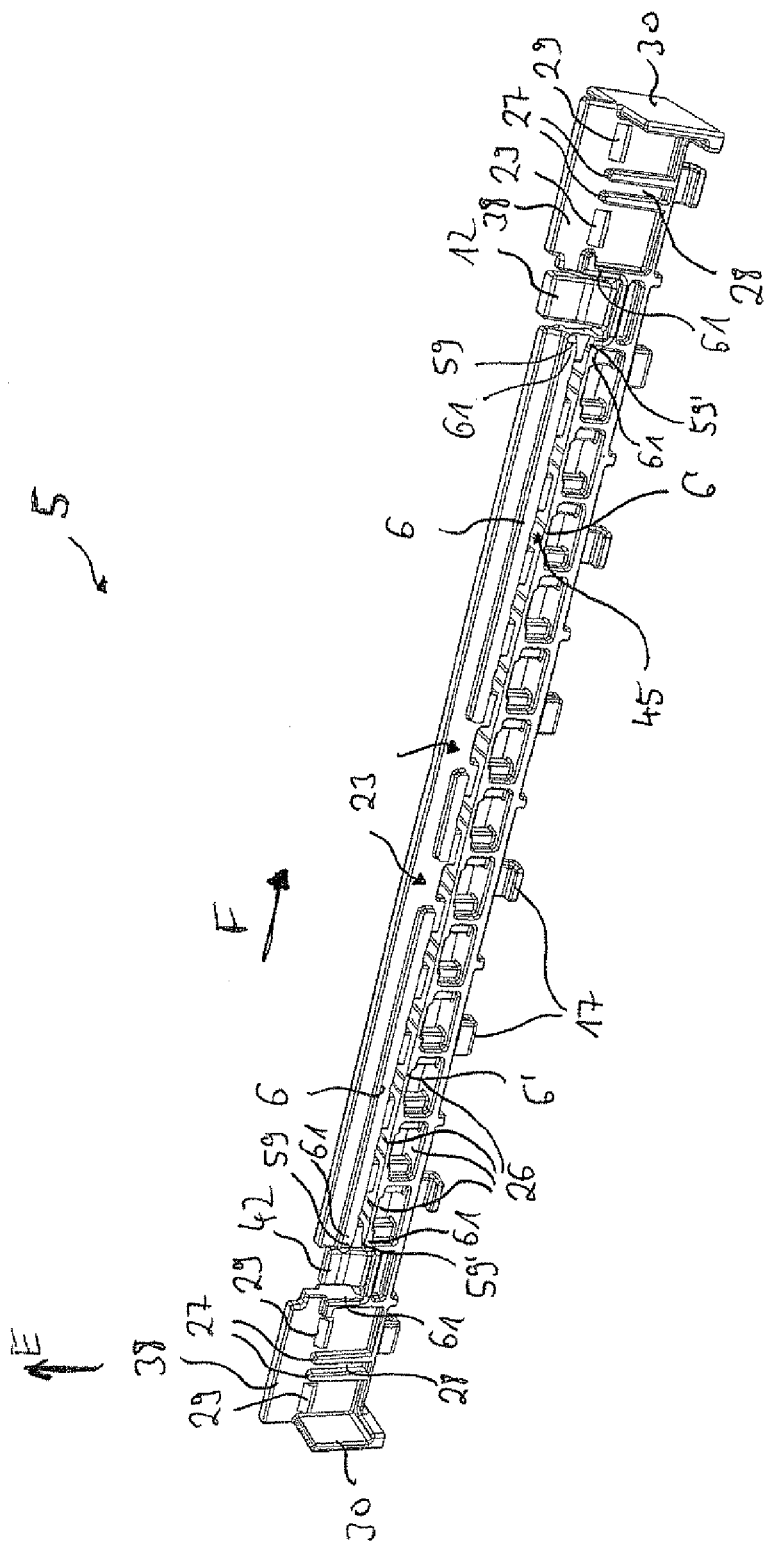
FIG. 6 shows the first main body according to FIG. 5 in a second perspective view.

Extending on each side from the middle piece 48 are an upper guide rail 6 and a lower guide rail 6', of which only one can be seen here; the opposite side of the middle piece 48 with the two other guide rails 6, 6' is shown in FIG. 6. The upper guide rail 6 and the lower guide rail 6' extend along the longitudinal extent of the main body 5 and define a guide direction F along which a carrier with an inserted bone screw is movable. As is explained in detail further below, a carrier for a bone screw can be removed in a removal direction E extending perpendicular to the guide direction F.

A space 45 is formed between the upper guide rail 6 and the lower guide rail 6'. In this space 45, and also underneath the lower guide rail 6', the middle piece 48 contains a multiplicity of rinse openings 26, which allow a cleaning and/or sterilizing fluid to pass through. Below the rinse openings, several holding hooks 17 extend from the middle piece 48 and allow the main body 5 to be secured to the holding openings 18 of the main stand 46 of the storage unit 1.

The upper guide rails 6 have a bevel 59 on their underside at both ends. The lower guide rails 6' have a bevel 59' on their top face at both ends. Adjacent to the locking tongue 42 and to the holding spring 12, the main body 5 has lateral mating contact areas 61 which, by contact with the contact areas 60 of a carrier 2 (cf. FIG. 3b), prevent tilting of the carrier 2 in the receiving area 14 or in the removal area 8 (cf. description in connection with FIGS. 9 and 11 below).

In the area of one end of the main body 5, an elastic holding spring 12 is arranged between the middle piece 48 and the intermediate piece 38 and extends in the removal direction E. The holding spring 12 has a lateral projection 54, on the underside of which a bevel 39 is formed. The position of the holding spring 12 defines a removal area 8 of the storage unit 1, in which area a carrier 2 can be removed from the storage unit 1.

In the area of the opposite end of the main body 5, an elastic locking tongue 42 is arranged between the middle piece 48 and the intermediate piece 38 and extends in the removal direction E. The locking tongue 42 has a lateral projection 55. A bevel 49 is formed on the top face of the projection 55, while a locking surface 43 is formed on the underside. This locking surface 43 extends substantially perpendicular to the removal direction E. The position of the locking tongue 42 defines a receiving area 14 of the storage unit 1, in which area a carrier 2 can be received by the storage unit 1.

The two intermediate pieces 38 have, on each side, two parallel first guide projections 27, which extend with their longitudinal direction parallel to the removal direction. A guide groove 28 is formed between the two first guide projections 27. Each of the two intermediate pieces 38 also has, on each of its sides, two first locking projections 29.

FIG. 6 shows another perspective view of the main body 5 from FIG. 5, the opposite side of said main body 5 being seen here. This opposite side also has an upper guide rail 6 and a lower guide rail 6'. However, the upper guide rail 6 is interrupted by two breaks 23. On the side of the main body 5 that can be seen in FIG. 6, the holding springs 12 and the locking tongue 42 have no projections.

The upper guide rails 6 on this side of the main body 5 also have a bevel 59 on their underside at both ends. The lower guide rails 6' have a bevel 59' on their top face at both ends. Adjacent to the locking tongue 42 and to the holding spring 12, the main body 5 has lateral mating contact areas 61 which, by contact with the contact areas 60 of a carrier 2 (cf. FIG. 3*b*), prevent tilting of the carrier 2 in the receiving area 14 or in the removal area 8 (cf. description in connection with FIGS. 9 and 11 below).

Figure 7:
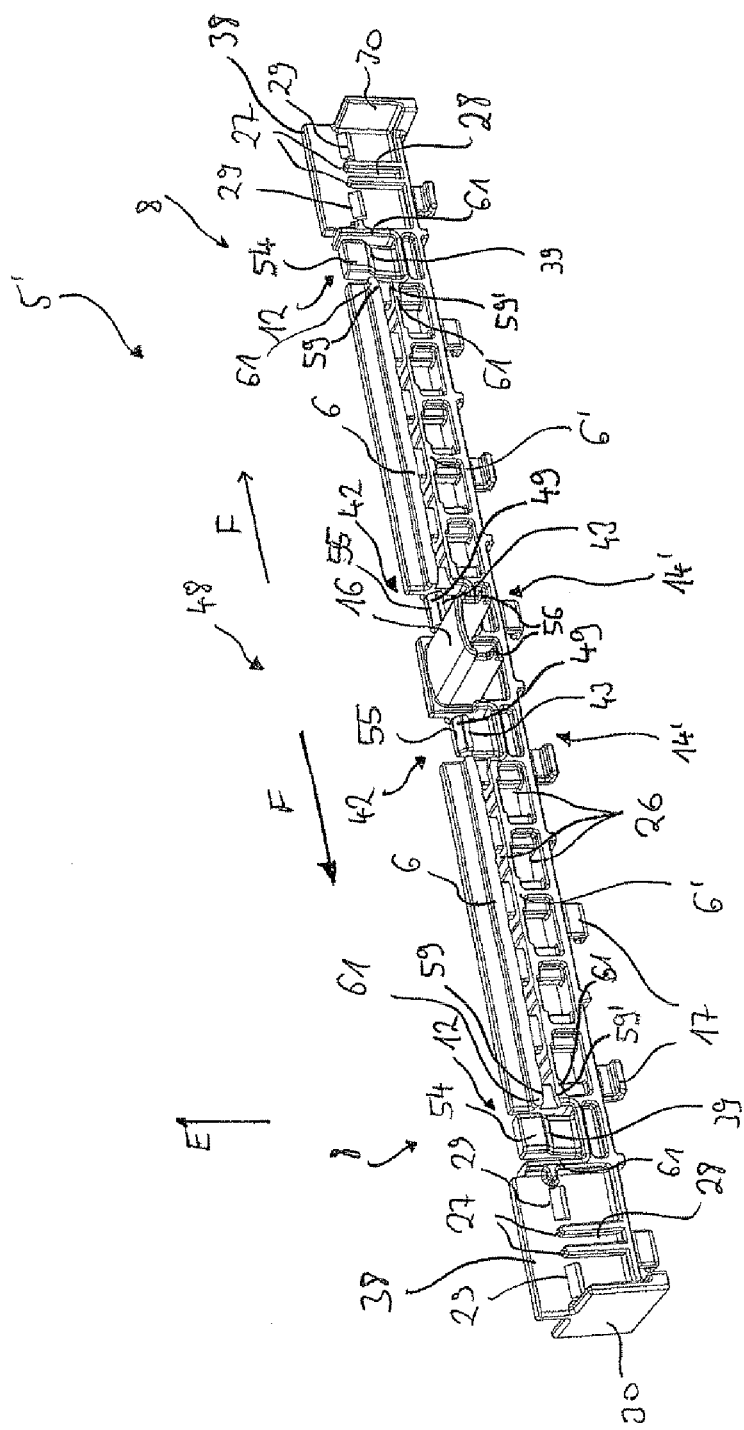
FIG. 7 shows a second main body of the storage unit in a first perspective view.

FIG. 7 shows a perspective view of one of the two second main bodies 5' of the storage unit 1. In contrast to the first main body 5, the second main body 5' has a separating element 16 in the middle area. The separating element 16 interrupts the middle piece 48 and therefore also the upper guide rails 6 and also the lower guide rails 6'. The separating element 16 has two positioning pins 56 that can be brought into engagement with a positioning groove 57 of an adjacent further main body 5' (cf. also FIG. 8 below). The area of the guide rails 6, 6' shown on the left in FIG. 7 defines a first guide direction F, while the area of the guide rails 6, 6' shown on the right defines a second guide direction F', which runs counter to the first guide direction F.

Alongside the separating element 16, an elastic locking tongue 42 is also arranged in the first guide direction F and also in the second guide direction F', which locking tongue 42 extends in the removal direction E. The locking tongue 42 has a lateral projection 55. A bevel 49 is formed on the top face of the projection 55, while a locking surface 43 is formed on the underside. This locking surface 43 extends substantially perpendicular to the removal direction E. The positions of the locking tongues 42 define receiving areas 14' of the storage unit 1, in which areas carriers can be received by the storage unit 1. Elastic holding springs 12 are arranged between the middle piece 48 and the intermediate pieces 38. Each of these two holding springs 12 has a lateral projection 54, on the underside of which a bevel 39 is formed. The positions of the holding springs 12 define removal areas 8 of the storage unit 1, in which areas a carrier 2 can be removed from the storage unit 1.

The upper guide rails 6 have a bevel 59 on their underside at both ends. The lower guide rails 6' have a bevel 59' on their top face at both ends. Adjacent to the holding springs 12, the main body 5' has lateral mating contact areas 61 which, by contact with the contact areas 60 of a carrier 2 (cf. FIG. 3*b*), prevent tilting of the carrier 2 in the removal areas 8 (cf. description in connection with FIGS. 9 and 11 below).

Figure 8:
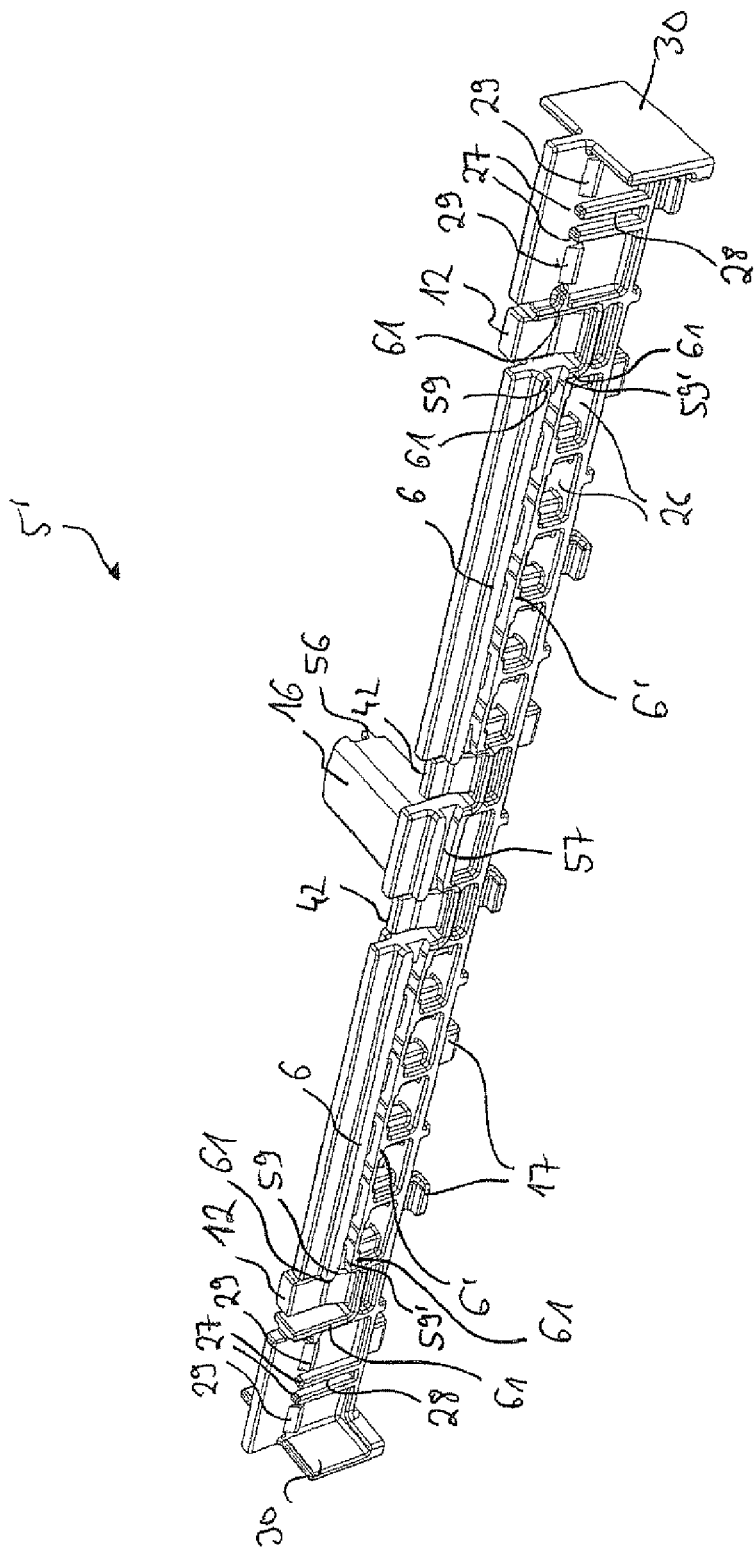
FIG. 8 shows the second main body according to FIG. 7 in a second perspective view.

FIG. 8 shows another perspective view of the main body 5', the opposite side of the latter being seen here. This opposite side has, in a middle area, a positioning groove 57 with which positioning pins 56 of an adjacent main body 5' can be brought into engagement, as can be seen in FIG. 4.

The upper guide rails 6 on this side of the main body 5' also have a bevel 59 on their underside at both ends. The lower guide rails 6' have a bevel 59' on their top face at both ends. Adjacent to the holding springs 12, the main body 5' has lateral mating contact areas 61 which, by contact with the contact areas 60 of a carrier 2 (cf. FIG. 3*b*), prevent tilting of the carrier 2 in the removal areas 8 (cf. description in connection with FIGS. 9 and 11 below).

In FIG. 9, the storage unit 1 is shown in a sectional side view along the line IX from FIG. 2, but with the omission, for reasons of clarity, of the main body 5' shown at the bottom in FIG. 2 and of the lower row of carriers 2 in FIG. 2. According to FIG. 9, a bone screw 3 is inserted in the carrier 2 and is held by the holding tongue 21 of the carrier 2.

The carrier 2, with the bone screw 3 inserted therein, is arranged between the locking tongue 42 of the main body 5 and the holding spring 12 of the main body 5'. The carrier 2 with bone screw 3 can be inserted from above into the position shown in FIG. 8. In doing so, the locking tongue 42 is bent laterally aside, when the underside of the left-hand guide projection 22 of the carrier 2 makes contact with the bevel 49 on the top face of the locking tongue 42, and then engages over the guide projection 22. By means of the locking tongue 42, the carrier 2 is then clamped laterally. The top face of the left-hand guide projection 22 of the carrier 2 is in contact with the locking surface 43 of the locking tongue 42. This prevents the carrier 2 from being removed upwardly in the vertical direction and also prevents the carrier 2 from accidentally falling out when the storage unit 1 is tilted. Therefore, a receiving area 14 for the carrier 2 is present in this area.

In the position shown in FIG. 9, the contact areas 60 of the carrier 2 (cf. FIG. 3*b*) are in contact with the mating contact areas 61 of the guide rails 6, 6' (cf. FIGS. 5 to 8). These contact areas and mating contact areas lie outside the plane of the drawing and for this reason cannot be seen in FIG. 9. This contact supports the carrier 2 and prevents the latter from tilting within the plane of the drawing.

During a movement of the carrier 2 in the guide direction, when the upper edges 58 and lower edges 58' (cf. FIGS. 3*a* and 3*b*) are in contact with the bevels 59, 59' on the guide rails 6, 6' (cf. FIGS. 5 to 8), the guide projections 22 are introduced into the space 45 between the guide rails 6, 6', as is shown in FIG. 10.

FIG. 10 shows a sectional side view along the line X from FIG. 2. The two guide projections 22 of the carrier 2 are now each located between an upper guide rail 6 and a lower guide rail 6'. In this area, the carrier 2 cannot be removed upward in the vertical direction from the storage unit 1, nor can it be inserted downward into the latter. The carrier 2 is therefore only movable along the guide direction F, which lies perpendicular to the plane of the drawing.

FIG. 11 finally shows a sectional side view along the line XI from FIG. 2. The carrier 2 is arranged between two holding springs 12 and is laterally clamped by the left-hand holding spring 12. The top face of the left-hand guide projection 22 of the carrier 2 is in contact with the bevel 39 on the left-hand holding spring 12. Due to the tension of the holding spring 12, the carrier 2 is secured against falling out of the storage unit 1, even if the storage unit 1 is accidentally tilted. The carrier in FIG. 11 is therefore located in a holding position H.

In the position shown in FIG. 11, and in the same way as has been explained in connection with FIG. 9, the contact areas 60 of the carrier 2 (cf. FIG. 3b) are in contact with the mating contact areas 61 of the guide rails 6, 6' (cf. FIGS. 5 to 8). These contact areas and mating contact areas lie outside the plane of the drawing and cannot therefore be seen in FIG. 11. This contact supports the carrier 2 and prevents its tilting within the plane of the drawing.

From the holding position H shown in FIG. 11, the carrier 2 can be brought to a release position L by actuation of a release part 4, such that it can be removed in the removal direction E, as is explained below. Thus, a removal area 8 is shown in FIG. 11.

Figure 12:
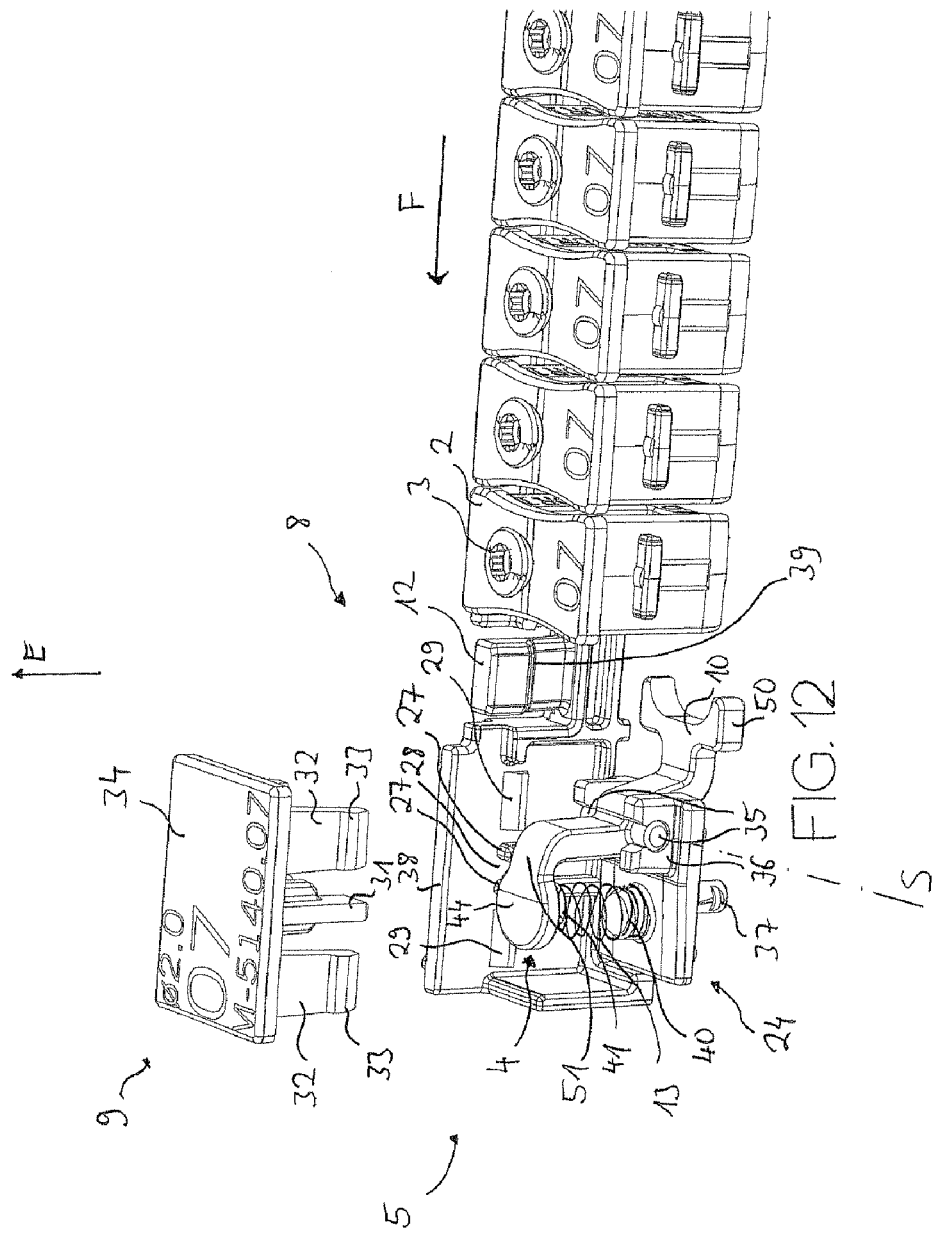
FIG. 12 shows a perspective view of the removal area with a release part and an actuating element.

The removal area 8 is reproduced in detail in FIG. 12, but initially without the carrier 2 shown in FIG. 11. A base part 24 is arranged next to the intermediate piece 38 of the main body 5. On its underside, the base part 24 has two holding pins 37, with which it can be inserted into corresponding openings 25 of the main stand 46 (cf. FIG. 1 above). A first holding projection 40 is arranged on the top face of the base part 24.

A release part 4 is pivotably connected to the base part 24. For this purpose, the release part 4 has mutually opposite rotation pins 35, which engage in corresponding bearings 36 of the base part 24. The release part 4 is thus pivotable relative to the base part 24 about a pivot axis S, which is perpendicular to the guide direction F and also to the removal direction E. Since both the main body 5 and also the base part 24 are secured on the main stand 46 (not shown here), the release part 4 is therefore also pivotable relative to the main body 5.

The release part 4 is designed basically as a two-armed lever. On the lower side, it has a fork-shaped first lever arm 50 with an upwardly directed first contact surface 10. The upper, second lever arm 51 has a top face 44 and, lying opposite this, a second holding projection 41. Arranged between the first holding projection and the second holding projection there is a tension spring 13, which holds the release part 4 in the position shown. In this way, the release part 4 is supported relative to the base part 24.

The actuating element 9 has a cover plate 34, which contains an identification of the bone screws 3 that are held by the associated carriers 2. Four locking tongues 32, of which only two can be seen here, extend from the underside of the cover plate 34. Second locking projections 33 are formed at the end of the locking tongues 32. Moreover, two second guide projections 31, of which only one can be seen here, extend downward from the cover plate 34.

To achieve the position shown in FIG. 1, the actuating element 9 is placed downward over the release part 4. The two second guide projections not visible here on one side of the actuating element 9 then engage in the guide grooves 28 of the main body 5, while the two visible second guide projections 31 on the second side of the actuating element 9 engage in the guide grooves of a second main body 5' not shown here. In this way, the actuating element 9 is guided linearly in the vertical direction, that is to say parallel to the removal direction E. Moreover, the second locking projections 33 of the actuating element 9 engage behind the first locking projections 29 on the intermediate pieces 38 of the main bodies 5, 5'.

To move a carrier 2 from a holding position to a release position, the actuating element 9 is actuated by being pressed down vertically. The underside of the cover plate 34 then presses the second lever arm 51 of the release part 4 down counter to the force of the tension spring 13. As a result of this, the first lever arm 50 of the release part 4 is raised and presses a carrier (not shown here) upward in the removal direction E counter to the spring force of the holding spring 12 (cf. FIGS. 13 and 14 below). In this way, the carrier is moved from the holding position to the release position, in which it can be released from the storage unit 1 in the removal direction E.

It is therefore not necessary to grip the carrier 2 directly with the fingers or with forceps in order to move it from the holding position to the release position. This would be very cumbersome because of the small dimensions of the carrier and would also require there to be much more space around the carrier 2 in order to be able to grip the latter at all from the sides. Since the carrier 2 is moved upward, it protrudes above the adjacent carriers 2 and can therefore be gripped much more easily, and without any significant tensile force being needed to grip it.

Figure 13:
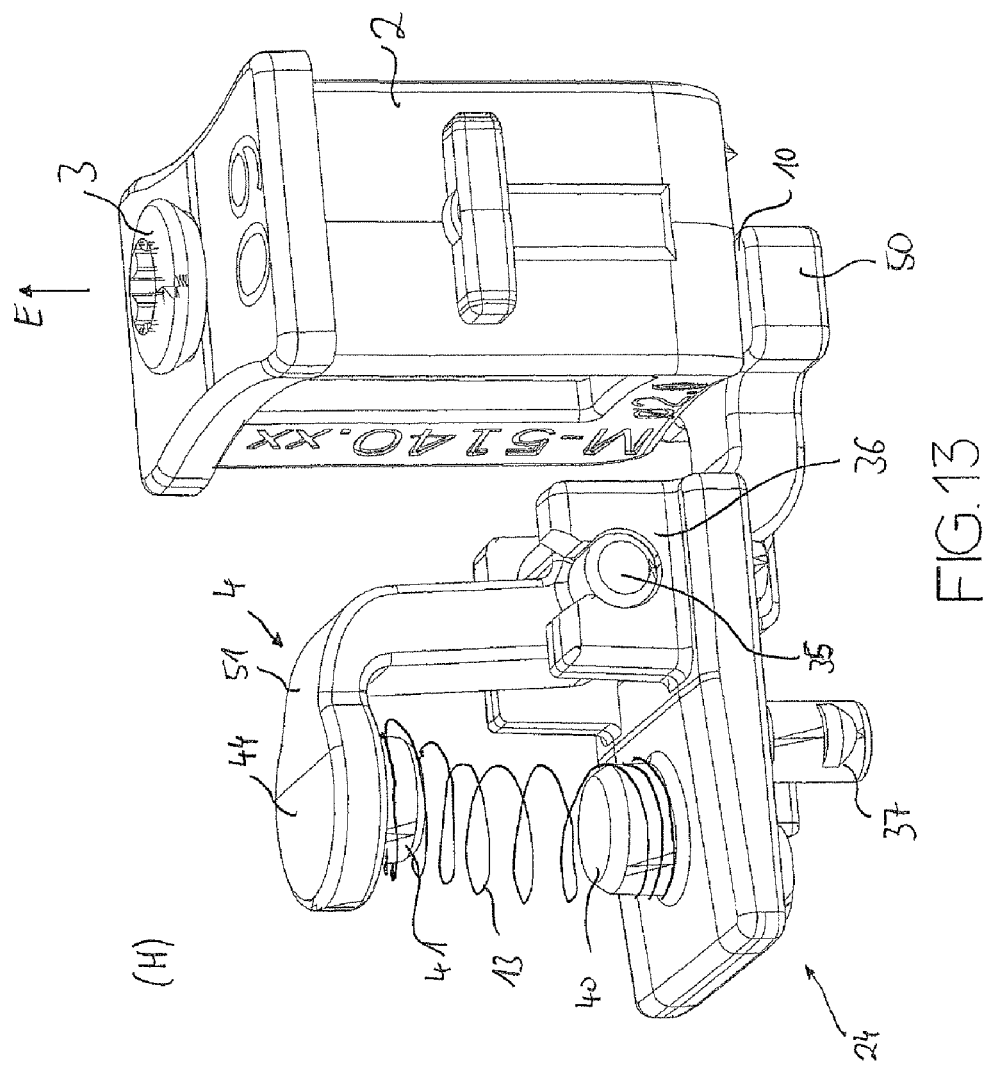
FIG. 13 shows the release part, a base part and a carrier with a bone screw in a first perspective view.
Figure 14:
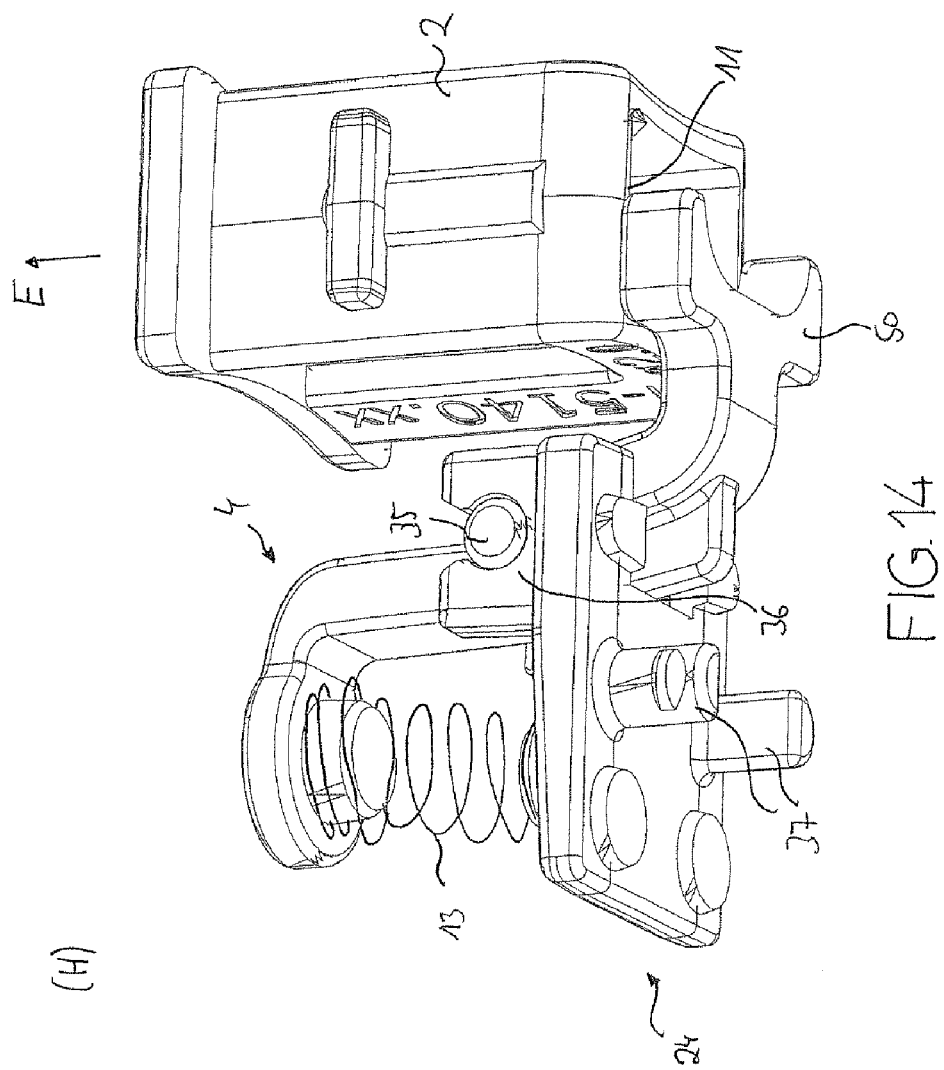
FIG. 14 shows the release part, the base part and the carrier with a bone screw in a second perspective view.
Figure 15:
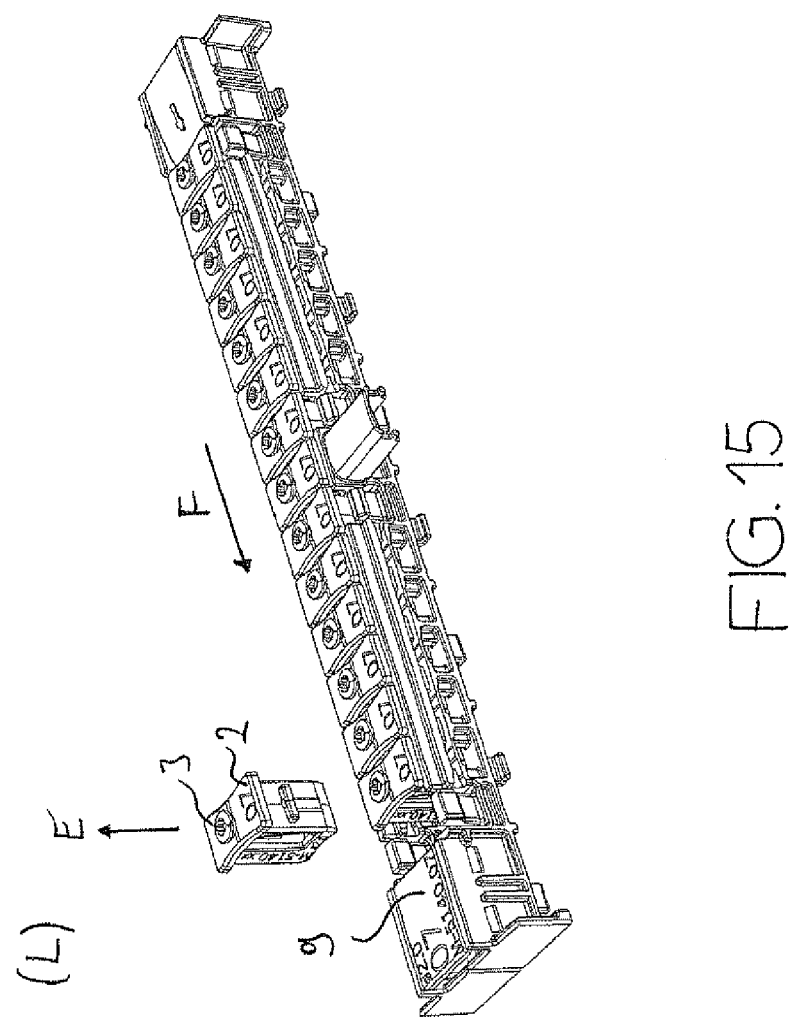
FIG. 15 shows a perspective view of part of the storage unit with a carrier removed.

The perspective views in FIGS. 13 and 14 show the release part 4 and the base part 24 together with a carrier 2 and with a bone screw 3 received in the latter. The first contact surface on the first lever arm of the release part 4 presses from below onto a second contact surface 11, which is arranged on the underside of the carrier 2. In this way, the carrier can be transferred from the holding position H shown in FIGS. 13 and 14 to the release position L shown in FIG. 15. The carrier 2 can then be removed in a removal direction E, which is perpendicular to the guide direction F.

The release part 4, the base part 24 and the actuating element can be made of PPSU or PEEK and can be produced, for example, by injection molding. In the illustrative embodiment shown here, the release part 4 measures 10 mm×6.5 mm×12 mm. The base part 24 measures 11 mm×9.5 mm×6 mm. The actuating element 9 measures 12 mm×9 mm×6 mm.

The invention claimed is:

1. The surgical item container set containing:
   at least one storage unit for storing and/or making available at least one carrier for at least one surgical item, and
   at least one carrier for at least one surgical item,
   wherein the carrier can be brought to a holding position and to a release position, the carrier being held by the storage unit in the holding position and being released or releasable from the storage unit in the release position,
   the storage unit has at least one release part, and the carrier can be brought from the holding position to the release position by actuation of the release part, thereby allowing the carrier to be removed from the storage unit,
   the storage unit has at least one guide rail along which the carrier is arranged to be movable in a guide direction,
   the storage unit is designed in such a way that the carrier, in the release position, can be released from the storage unit by movement in a removal direction which is substantially perpendicular to the guide direction,
   the storage unit is designed in such a way that only in a removal area, which forms a part of the storage unit, can the carrier be brought from the holding position to the release position by actuation of the release part,
   the removal area is arranged in an end area of the guide rail,
   the guide rail contains only a single removal area, this single removal area is arranged in the end area of the guide rail, and only in this single removal area, the carrier can be brought from the holding position to the release position by actuation of the release part, and
   the surgical item container set further comprises an actuating element, upon actuation of which the release part is actuated, and the actuating element comprises a cover plate which shows information identifying the surgical item.

2. The surgical item container set according to claim 1, wherein the storage unit has at least one main body, in relation to which the release part is movable.

3. The surgical item container set according to claim 1, wherein the release part is arranged in an end area of the guide rail.

4. The surgical item container set according to claim 1, wherein the storage unit is designed in such a way that, upon actuation of the release part, the carrier can be brought from the holding position to the release position on account of a direct contact between the carrier and the release part.

5. The surgical item container set according to claim 4, wherein the carrier can be brought from the holding position to the release position on account of a direct contact between at least one first contact surface of the release part and at least one second contact surface of the carrier.

6. The surgical item container set according to claim 1, comprising at least one receiving area in which the carrier can be received by the storage unit.

7. The surgical item container set according to claim 1, wherein at least one of the carriers is received by the storage unit.

8. The surgical item container set according to claim 1, wherein the release part is or can be connected directly or indirectly, in a movable manner, to the actuating element in such a way that, upon actuation of the actuating element, the release part is actuated.

9. The surgical item container set according to claim 1, wherein at least one locking tongue extends from an underside of the cover plate for locking the cover plate to a main body of the surgical item container set.

10. The surgical item container set according to claim 9, wherein a second locking projection is formed at the end of the locking tongue and the main body comprises at least a first locking projection, and the second locking projection of the actuating element engages behind the first locking projection of the main body.

11. The surgical item container set according to claim 1, wherein at least one second guide projection extends downward from the cover plate.

12. The surgical item container set according to claim 11, wherein the second guide projection engages in a guide groove of a main body of the surgical item container set.

13. The surgical item container set according to claim 12, wherein the second guide projection and the guide groove are arranged such that the actuating element is guided linearly in a direction parallel to a removal direction in which the carrier, in the release position, can be released from the surgical item container set.

14. The surgical container, containing
at least one storage unit for storing and/or making available at least one carrier for at least one surgical item and/or
at least one set, the set containing
at least one storage unit for storing and/or making available at least one carrier for at least one surgical item and
at least one carrier for at least one surgical item,
wherein the carrier can be brought to a holding position and to a release position, the carrier being held by the storage unit in the holding position and being released or releasable from the storage unit in the release position,
the storage unit has at least one release part, and the carrier can be brought from the holding position to the release position by actuation of the release part, thereby allowing the carrier to be removed from the storage unit,
the storage unit is designed in such a way that only in a removal area, which forms a part of the storage unit, can the carrier be brought from the holding position to the release position by actuation of the release part,
the storage unit has a guide rail along which the carrier can move,
the removal area is arranged in an end area of the guide rail,
the guide rail contains only a single removal area, this single removal area is arranged in the end area of the guide rail, and only in this single removal area, the carrier can be brought from the holding position to the release position by actuation of the release part, and
the storage unit further comprises an actuating element, upon actuation of which the release part is actuated, and the actuating element comprises a cover plate which shows information identifying the surgical item.

15. The surgical container according to claim 14, containing at least one of said set containing at least one storage unit for storing and/or making available at least one carrier for at least one surgical item and at least one carrier for at least one surgical item.

16. The surgical container according to claim 15, further comprising at least one surgical item which is inserted into said carrier.

17. The surgical container according to claim 16, wherein the surgical item is a bone screw.

18. The surgical container according to claim 14, wherein the release part is or can be connected directly or indirectly, in a movable manner, to the actuating element in such a way that, upon actuation of the actuating element, the release part is actuated.

19. The surgical container according to claim 14, wherein at least one locking tongue extends from an underside of the cover plate for locking the cover plate to a main body of storage unit.

20. The surgical container according to claim 19, wherein a second locking projection is formed at the end of the locking tongue and the main body comprises at least a first locking projection, and the second locking projection of the actuating element engages behind the first locking projection of the main body.

21. The surgical container according to claim 14, wherein at least one second guide projection extends downward from the cover plate.

22. The surgical container according to claim 21, wherein the second guide projection engages in a guide groove of a main body of the storage unit.

23. The surgical container according to claim 22, wherein the second guide projection and the guide groove are arranged such that the actuating element is guided linearly in a direction parallel to a removal direction in which the carrier, in the release position, can be released from the storage unit.

* * * * *